United States Patent
Amit

(10) Patent No.: US 8,887,551 B2
(45) Date of Patent: Nov. 18, 2014

(54) CALIBRATION OF INSTRUMENT RELATIVE TO ULTRASONIC PROBE

(75) Inventor: Dan Amit, Kiryat Motzkin (IL)

(73) Assignee: Trig Medical Ltd., Nesher (IL)

( * ) Notice: Subject to any disclaimer, the term of this patent is extended or adjusted under 35 U.S.C. 154(b) by 144 days.

(21) Appl. No.: 13/225,576

(22) Filed: Sep. 6, 2011

(65) Prior Publication Data
US 2013/0055788 A1    Mar. 7, 2013

(51) Int. Cl.
    *G01N 29/00*    (2006.01)
(52) U.S. Cl.
    USPC ........................................................ 73/1.82
(58) Field of Classification Search
    USPC ........................ 73/1.75, 1.79, 1.82
    See application file for complete search history.

(56) References Cited

U.S. PATENT DOCUMENTS

| | | | | |
|---|---|---|---|---|
| 5,647,373 A | * | 7/1997 | Paltieli | 600/567 |
| 6,138,495 A | * | 10/2000 | Paltieli et al. | 73/1.86 |
| 6,216,029 B1 | * | 4/2001 | Paltieli | 600/427 |
| 6,311,540 B1 | * | 11/2001 | Paltieli et al. | 73/1.82 |
| 6,604,404 B2 | * | 8/2003 | Paltieli et al. | 73/1.82 |
| 7,090,639 B2 | * | 8/2006 | Govari | 600/437 |
| 7,867,167 B2 | * | 1/2011 | Boctor et al. | 600/437 |
| 8,391,571 B2 | * | 3/2013 | Cinquin et al. | 382/128 |

* cited by examiner

*Primary Examiner* — Hezron E Williams
*Assistant Examiner* — David Z Huang
(74) *Attorney, Agent, or Firm* — Dekel Patent Ltd.; David Klein

(57) ABSTRACT

A method of calibration including placing an instrument on an arbitrary point and at an arbitrary rotational orientation on an ultrasonic probe, obtaining spatial coordinates of the instrument, obtaining spatial coordinates of three points on an external surface of the ultrasonic probe, and using the three points to define an ultrasonic image plane, obtaining spatial coordinates of a set of landmarks which have a known spatial relationship to the ultrasonic image plane, these landmarks defining a direction in which the ultrasonic probe is directed within the ultrasonic image plane, and obtaining spatial coordinates of a front point on a front facing surface of the ultrasonic probe, the front facing surface having a known relation with a reference axis of a scanning plane of the ultrasonic probe that defines where an ultrasonic image starts within the ultrasonic image plane.

8 Claims, 3 Drawing Sheets

CALIBRATION OF INSTRUMENT RELATIVE TO ULTRASONIC PROBE

FIELD OF THE INVENTION

The present invention relates generally to calibrating the location and orientation of a sensor with respect to the beam plane (scanning plane) of an ultrasound scanning transducer.

BACKGROUND OF THE INVENTION

Many medical systems are used for guiding instruments by means of position sensors and ultrasonic probes. For example, U.S. Pat. No. 6,216,029 to Paltieli describes a system with a position sensor on an ultrasonic probe, which is used in conjunction with a needle, or other insertion device, on which another position sensor is attached. The absolute location and orientation of the plane displayed by the imaging system is determined by the position sensor on the ultrasonic probe (also called ultrasonic transducer, the terms being used interchangeably). The system enables the measurement of the relative location and orientation of the needle with respect to target tissue. Once the spatial data are determined, it is possible to derive the expected path of the needle towards the target and to display it on the image in order to enable the physician to navigate the needle precisely towards the target.

In such a system, the needle position sensor, secured to a predetermined point on the needle, measures the precise location and orientation of the needle upper tip but the ultrasonic position sensor, being attached to the ultrasonic transducer at a convenient, arbitrary location thereon, does not have a well determined spatial position and orientation to the scan plane of the transducer so as to precisely relate the transducer position sensor to the transducer scan plane. Yet, since the navigation of the needle to the target uses the ultrasound image as a background for the display of the future path of the needle, it is imperative to calculate the precise location and orientation of the scan plane with respect to the position sensor on the ultrasound transducer.

U.S. Pat. No. 6,604,404 to Paltieli et al. describes systems for calibrating a first position measuring component on an imaging or scanning transducer with respect to the scanning plane. Calibrations are performed by using a calibrating device including an additional or second position measuring component, such that during the calibration process, the relative position of between these position measuring components can be calculated. Calibrations are also performed by viewing targets on the scanning plane that are at a known position with respect to the second position measuring component. Calibrations are also performed based on the scanning plane and position measuring component on a guided device, such as a needle, that typically is used in conjunction with the imaging or scanning transducer.

SUMMARY OF THE INVENTION

The present invention seeks to provide improved methods for calibrating the position and orientation of the position sensor mounted on the ultrasonic probe, as is described more in detail hereinbelow.

There is thus provided in accordance with an embodiment of the present invention a method of calibration including placing an instrument (e.g., a position sensor, transmitter or other electromagnetic or optical device) on an arbitrary point and at an arbitrary rotational orientation on an ultrasonic probe, the ultrasonic probe having known dimensions that describe its geometrical shape, obtaining spatial coordinates of the instrument, obtaining spatial coordinates of three points on an external surface of the ultrasonic probe, and using the three points to define an ultrasonic image plane, obtaining spatial coordinates of a set of landmarks which have a known spatial relationship to the ultrasonic image plane, the spatial coordinates of the landmarks defining a direction in which the ultrasonic probe is directed within the ultrasonic image plane, and obtaining spatial coordinates of a front point on a front facing surface of the ultrasonic probe, the front facing surface having a known relation with a reference axis of a scanning plane of the ultrasonic probe that defines where an ultrasonic image starts within the ultrasonic image plane.

In accordance with an embodiment of the present invention, the instrument includes a position sensor, and obtaining the spatial coordinates of the position sensor is done from data received from the position sensor.

In accordance with an embodiment of the present invention obtaining the spatial coordinates of the points on the external surface of the ultrasonic probe is done from data received from a position sensor. The position sensor may touch the points or may sense the spatial coordinates of the points by non-contact sensing.

In accordance with an embodiment of the present invention obtaining spatial coordinates of the landmarks includes obtaining spatial coordinates of a first set of one or more points along one side of the ultrasonic probe and an additional set of one or more points, symmetrical to the first set of one or more points, along the other side of the ultrasonic probe. Three of the points of the sets of points used for determining the direction may be the same three points obtained on the external surface of the ultrasonic probe for determining the ultrasonic image plane.

BRIEF DESCRIPTION OF THE DRAWINGS

The present invention will be understood and appreciated more fully from the following detailed description, taken in conjunction with the drawing in which.

DETAILED DESCRIPTION OF EMBODIMENTS

Figure 1:
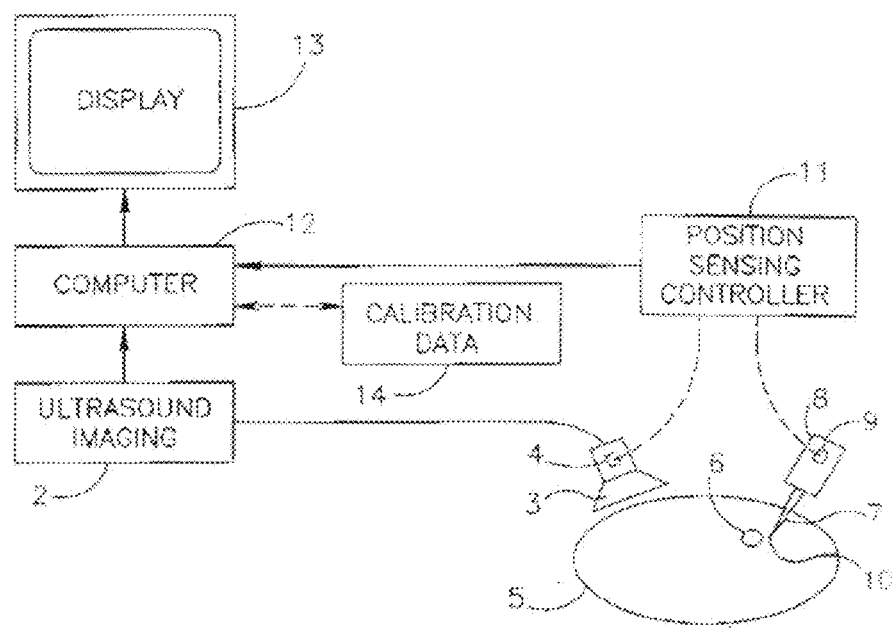
FIG. 1 is a simplified illustration of a prior art guiding imaging system (from U.S. Pat. No. 6,604,404) in which the calibration methods of the present invention are particularly useful.

Reference is now made to FIG. 1, which illustrates a prior art guiding imaging system (from U.S. Pat. No. 6,604,404) in which the calibration methods of the present invention are particularly useful.

The guiding system is used with an ultrasonic imaging system 2, which includes, without limitation, an ultrasonic probe (transducer) 3, on which a position sensor 4 (also referred to as a probe sensor 4) is mounted at a convenient, arbitrary spatial location and rotational orientation. The ultrasound transducer 3 is used for scanning a body 5 along scan planes through the body. For example, the body 5 (or body volume) may be tissue of a subject having a target 6 to which a needle 7 is to be directed in order to perform a biopsy. The needle 7 is carried by a needle holder 8 also having a position sensor 9 fixed to it. The location and orientation of the tip 10 of the needle 7 is precisely known beforehand with respect to the position sensor 9 carried by the needle holder 8, so that by detecting the location of the position sensor 9, the relative location and orientation of needle 7 with respect to the target tissue 6 can be calculated. The later calculation is executed in a position sensing controller 11.

Position sensing controller 11 also calculates the location and orientation of the ultrasound transducer sensor 4 and feeds the calculations to a computer 12. Computer 12 also receives an input from the ultrasonic imaging system 2, and computes the expected path of the needle 7 towards the target 6. This expected path is displayed on a display 13 to enable the physician to navigate the needle to the target 6 when taking a biopsy.

The position sensor 4 secured to the ultrasonic probe 3 does not have a well determined spatial relationship with the plane of the ultrasonic scanning plane. The present invention calibrates the location and orientation of the ultrasonic scanning plane with respect to position sensor 4 mounted on ultrasonic probe 3. The resultant data is used for calibration and is stored at 14 (preferably a database or memory device electronically linked to the computer 12).

Figure 2:
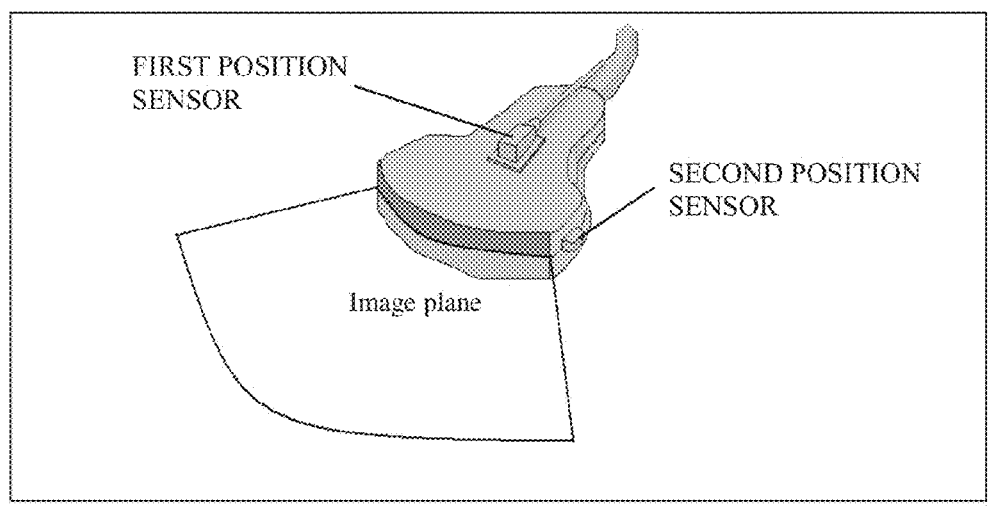
FIG. 2 is a simplified pictorial illustration of a position sensor mounted on an ultrasonic probe, in accordance with an embodiment of the present invention, and showing the imaging plane of the probe.

The ultrasonic probe 3 generates an acoustic beam that scans the tissue in front of the probe. This scanning is along a plane that is located in front of the probe as seen in FIG. 2. The calibration process is based on the assumption that the ultrasonic image plane is symmetric relative to the probe. The ultrasonic image is generated by acoustic echoes from within the scanning plane; thus the ultrasonic image is a section through this plane.

Since the probe sensor 4 is mechanically fixed on ultrasonic probe 3, a constant spatial relation is maintained between the (position and orientation of the) probe sensor 4 and the (position and orientation of the) ultrasound image plane. The present invention provides a method that enables to find this constant spatial relation and by using this relation, to calculate the exact position and orientation of the ultrasonic image based on the position and orientation of the probe sensor 4.

One embodiment of the calibration method is now described.

1. A first position sensor (e.g., probe sensor 4 of FIG. 1) is positioned on an arbitrary point and at an arbitrary rotational orientation on the ultrasonic probe (FIG. 2), e.g., probe 3 of FIG. 1. It is noted that the ultrasonic probe has known dimensions that describe its geometrical shape (including outer contour and all external surfaces). It is further noted that there are prior art sensors and probes wherein the probe has a predefined mounting location for the position sensor that establishes a predefined location and orientation of the sensor. Unlike the prior art, in the present invention, the position sensor can be mounted at any arbitrary location and orientation on the ultrasonic probe.

2. The spatial coordinates of the first position sensor are obtained, e.g., from data received from the first position sensor itself, which is connected to a suitable processor (well known in the art) for receiving and processing the data from position sensors to obtain the necessary coordinates.

3. From plane geometry, three points are required in order to define a plane. In order to find the ultrasonic image plane, three points must be measured. As mentioned previously, the ultrasonic image plane is assumed to be symmetric relative to the probe. Based on this assumption, the spatial coordinates of three points on an external surface of the ultrasonic probe can be used to define the ultrasonic image plane. These three points can be sensed (measured) by a second position sensor (seen in FIG. 3). The points can be on opposite sides of the probe or can be at other places.

The second position sensor can be a sensor that touches the points (e.g., accelerometer). Alternatively, the second position sensor may sense the spatial coordinates of the points by non-contact sensing (e.g., optical or IR sensors, capacitance or proximity sensors).

Figure 3:
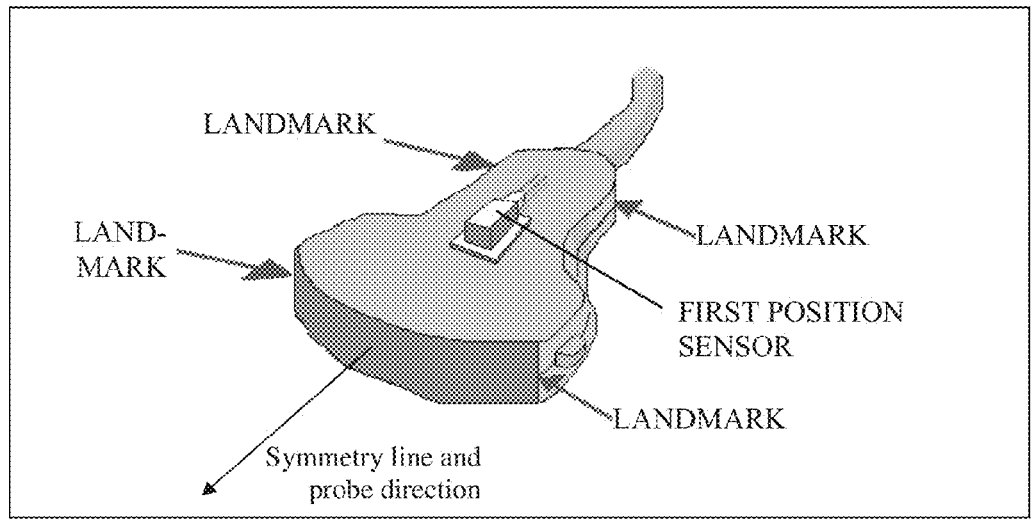
FIG. 3 is a simplified pictorial illustration of obtaining spatial coordinates of points on an external surface of the ultrasonic probe, in accordance with an embodiment of the present invention.

4. After determining the image plane, the direction in which the probe is directed within the image plane must be determined. This can be accomplished by obtaining the spatial coordinates of a first set of one or more points along one side of the probe and an additional set of one or more points, symmetrical to the first set of points, along the other side of the probe (as seen in FIG. 3). By taking the spatial coordinates of the first and second set of points, one can calculate the line of symmetry that passes through the center of the probe and this line provides us the information of probe direction (which is also the rotational orientation of the first position sensor with respect to the ultrasonic probe, that is, the "north-south" or "up-down" direction of the first position sensor).

It is noted that the points for determining the direction can be the same three points measured to determine the ultrasonic image plane. Thus, the step of determining the direction can be accomplished without measuring any additional points; alternatively it may be accomplished by measuring just one more additional point.

It is further noted that the invention is not limited to determining the line of symmetry that passes through the center of the probe. The direction can be determined by measuring on the probe body a set of landmarks which have a known spatial relationship to the image plane. The symmetry line is just one particular case of the invention. The measurement of the landmarks on the probe body can be made with a tool mounted on the measuring sensor, given that the spatial relationship between the tool and the sensor is known.

Figure 4:
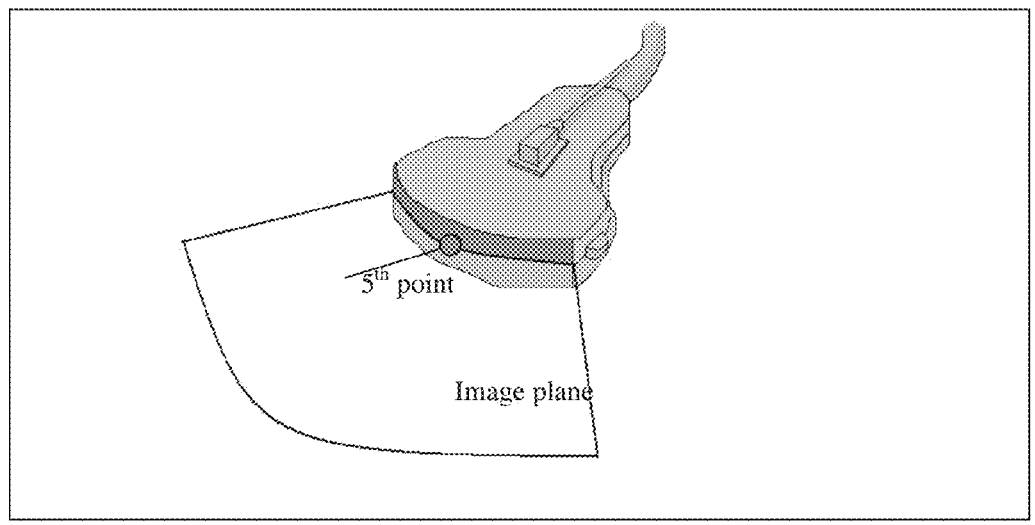
FIG. 4 is a simplified pictorial illustration of obtaining spatial coordinates of a front point on the front facing surface of the ultrasonic probe, in accordance with an embodiment of the present invention.
Figure 5:
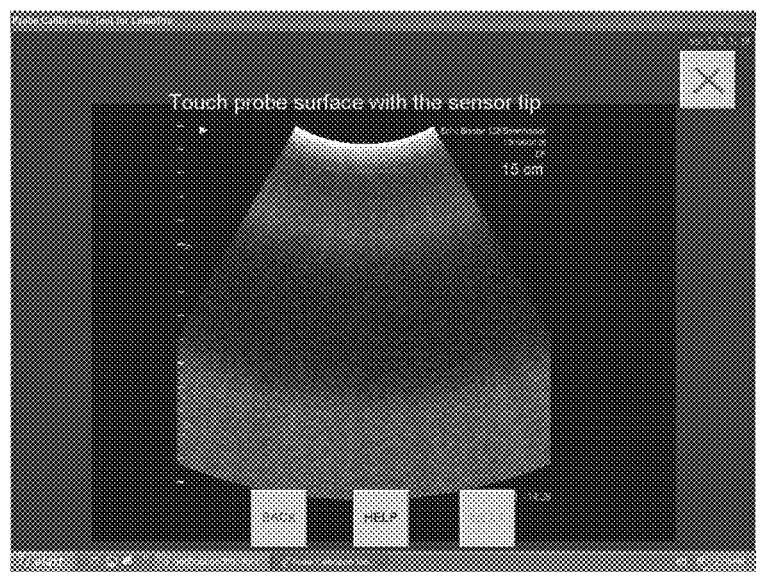
FIG. 5 is a simplified screen-shot illustration of an ultrasonic image made by the ultrasonic probe, showing the scanning plane of the ultrasonic probe, which is now calibrated with respect to the position sensor mounted on the ultrasonic probe, in accordance with an embodiment of the present invention.

5. The last piece of information needed is where the ultrasonic image starts within the known plane. This information can be acquired by measuring a point on the front area of the probe, e.g., at the center of the front area (FIG. 4).

In other words, the spatial coordinates of a front point on a front facing surface of the ultrasonic probe is obtained, e.g., from data received from the second position sensor. The front facing surface of the ultrasonic probe is the face or "window" that is placed on the object in order to obtain images. The front facing surface has a known relation with a reference axis of a scanning plane of the ultrasonic probe.

Afterwards, one can calculate exactly the position and orientation of the ultrasonic image by measuring the position and orientation of the probe sensor. It is noted that the front point on the front facing surface of the ultrasonic probe can be one of the three points that were measured to determine the ultrasonic image plane. Thus, the step of determining where the ultrasonic image starts within the known plane can be accomplished without measuring any additional points; alternatively it may be accomplished by measuring just one more additional point. Thus, the calibration can be accomplished by making three, four or five measurements.

In accordance with an embodiment of the present invention, the method further includes obtaining spatial coordinates of additional points on the external surface of the ultrasonic probe, repeating the determining steps and taking an average of the determining steps.

Although the embodiment above has been described for a position sensor mounted on the ultrasonic transducer, the calibration of the present invention is not limited to position sensors and is applicable for any kind of instrument mounted on the ultrasonic transducer. Such an instrument may include, without limitation, a transmitter used in a type of GPS system, or any other kind of electromagnetic or optical instrument used in position systems.

The scope of the present invention includes both combinations and subcombinations of the features described hereinabove as well as modifications and variations thereof which would occur to a person of skill in the art upon reading the foregoing description and which are not in the prior art.

What is claimed is:

1. For use with a position sensor secured to an ultrasonic probe, the ultrasonic probe having an ultrasonic image plane, a method for determining a spatial relation that is maintained between a position and orientation of the position sensor and a position and orientation of the ultrasonic image plane, the method comprising:

placing a position sensor at an arbitrary point and at an arbitrary rotational orientation on an ultrasonic probe, said ultrasonic probe having known dimensions that describe its geometrical shape;

obtaining spatial coordinates of said position sensor;

obtaining spatial coordinates of three points on an external surface of said ultrasonic probe, and using said three points to define an ultrasonic image plane, wherein the ultrasonic image plane is symmetric relative to said ultrasonic probe;

obtaining spatial coordinates of a set of landmarks which have a known spatial relationship to said ultrasonic image plane, said spatial coordinates of said landmarks defining a direction in which said ultrasonic probe is directed within said ultrasonic image plane;

obtaining spatial coordinates of a front point on a front facing surface of said ultrasonic probe, said front facing surface having a known relation with a reference axis of a scanning plane of said ultrasonic probe that defines where an ultrasonic image starts within said ultrasonic image plane, the spatial coordinates of the front point on the front facing surface of said ultrasonic probe and the direction in which said ultrasonic probe is directed within said ultrasonic image plane determining a spatial relation between the ultrasonic image plane and the front facing surface; and measuring the position and orientation of the probe sensor with respect to the front facing surface, and thereby determining the spatial relation maintained between the position sensor and the ultrasonic image plane.

2. The method according to claim 1, wherein obtaining the spatial coordinates of said position sensor is done from data received from said position sensor.

3. The method according to claim 1, wherein obtaining the spatial coordinates of said three points on the external surface of said ultrasonic probe is done from data received from another position sensor.

4. The method according to claim 3, wherein said position sensor touches said three points.

5. The method according to claim 3, wherein said position sensor senses the spatial coordinates of said three points by non-contact sensing.

6. The method according to claim 1, wherein determining the direction in which said ultrasonic probe is directed within the ultrasonic image plane is done by obtaining spatial coordinates of a first set of one or more points along one side of said ultrasonic probe and a second set of one or more points, symmetrical to the first set of points, along the other side of said ultrasonic probe, and calculating a line of symmetry that passes through a center of said ultrasonic probe, as defined by the spatial coordinates of the first and second set of points, wherein the line of symmetry determines the direction in which said ultrasonic probe is directed within the ultrasonic image plane.

7. The method according to claim 6, wherein three of the points of said sets of points used for determining the direction are the three points obtained on the external surface of said ultrasonic probe for determining the ultrasonic image plane.

8. The method according to claim 6, wherein the front point on the front facing surface of the ultrasonic probe is one of the three points used to define the ultrasonic image plane.

* * * * *